July 25, 1972 H. C. SWIM ET AL Plant Pat. 3,243
ROSE PLANT
Filed March 11, 1971
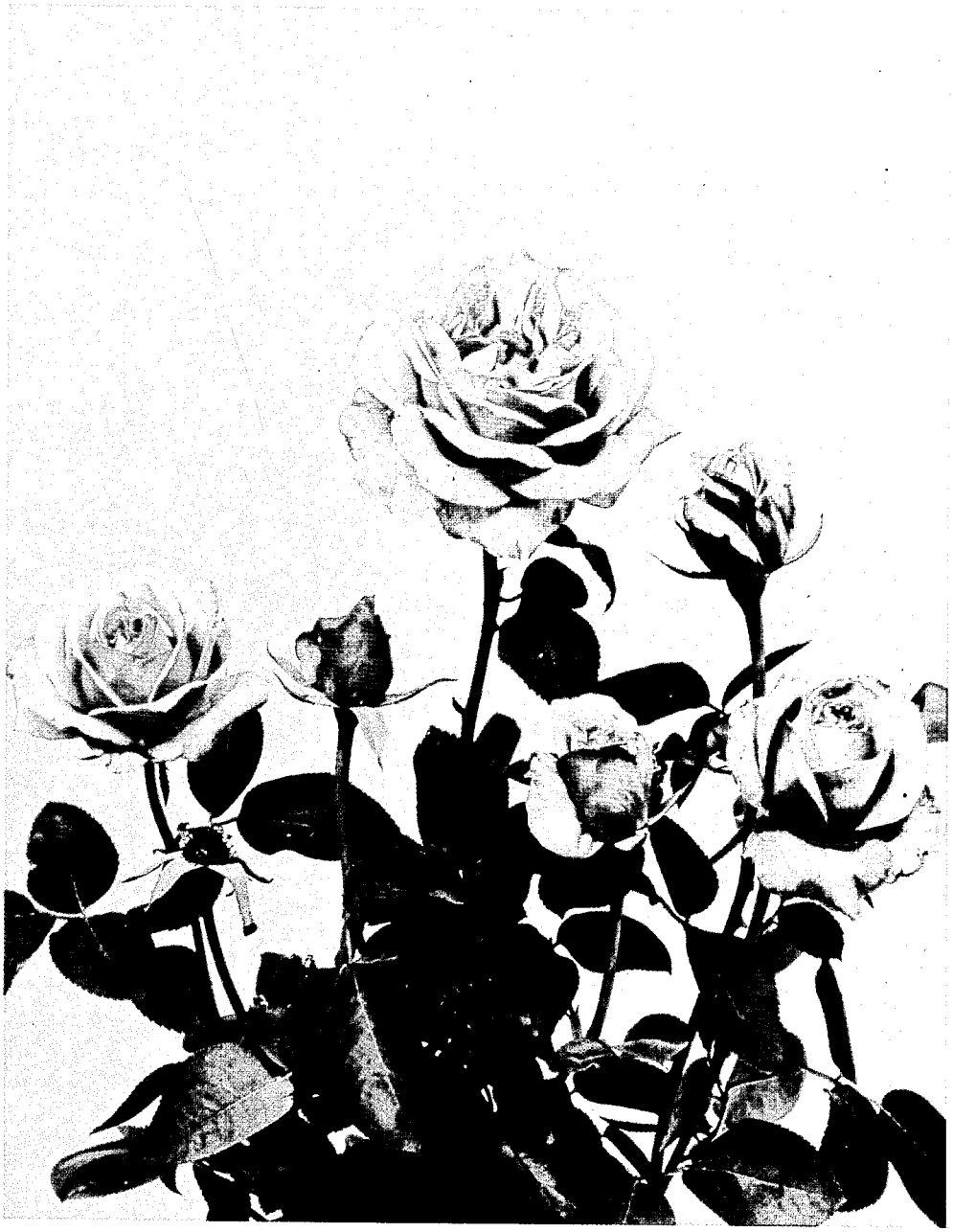
Inventors.
H. C. Swim
O. L. Meeks
By: Robb & Robb
Attorneys.

United States Patent Office

Plant Pat. 3,243
Patented July 25, 1972

3,243
ROSE PLANT

Herbert C. Swim and O. L. Weeks, Ontario, Calif., assignors to O. L. Weeks, doing business as Weeks Wholesale Rose Grower, Ontario, Calif.

Filed Mar. 11, 1971, Ser. No. 123,478
Int. Cl. A01h 5/00
U.S. Cl. Plt.—11 1 Claim The present invention relates to a new and distinct variety of rose plant of the hybrid tea class, which was originated by us by crossing two unnamed and unpatented rose seedlings, each having a rather complex breeding background involving both patented and unpatented rose varieties.

As the result of this breeding, we have produced a new and improved rose variety which is distinguished from its parents, as well as from all other rose varieties of which we are aware, as evidenced by the following unique combination of characteristics which are outstanding in the new variety:

(1) An especially well-branched, tall and symmetrical plant habit;

(2) Exceptionally good, heavy and semi-glossy foliage which clothes the plant well and which has excellent resistance to powdery mildew;

(3) Heavy stems of sufficient strength to hold all blooms erect, with a consequent pleasing compliment to the attractive foliage;

(4) Large flowers which are borne both singly and in clusters of 2 to 4 flowers with an occasional cluster of 5 flowers;

(5) A distinctive, attractive and unusual coral-orange flower color; and (6) A moderate and pleasing tea flower fragrance.

In comparison with its unnamed seed parent, the leaflets of our variety are broader and have better substance, and the foliage clothes the plant better; the flowers of the new variety are larger in size and have greater petalage; and the flowers are a bright coral-orange color as distinguished from the deep coral flower color of this parent.

As compared with its unnamed pollen parent, the plant of the new variety is larger and is better clothed with foliage as the result of having broader and longer leaflets; the leaflets have substantially more substance and are borne in compounds of 3, 5 and 7, while those of this parent are sometimes borne singly; the new variety has a normal complement of thorns, while the parent has few thorns; the flowers are essentially bright coral-orange in color, as compared with the bright red flower color of this parent; and the new variety has greater resistance to mildew.

Asexual reproduction of our new variety by budding, as performed at Chino, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Md., except where general color terms of ordinary dictionary significance are obvious:

Type: Hardy; tall: greenhouse and outdoor; for cut flowers and for garden decoration.

Class: Hybrid tea.

Breeding: Seedling.

*Seed parent.*—An unnamed seedling.

*pollen parent.*—An unnamed seedling.

Propagation: Holds its distinguishing characteristics through succeeding propagations by budding.

FLOWERS

Locality where grown and observed: Chino and Ontario, Calif.

Flowers borne: Singly and from 2 to 5 to stem; in irregular clusters; on stems of medium length and normal strength.

Quantity of bloom: From free to abundant, outdoors.

Continuity: From intermittent to continuous.

Fragrance: Moderate.

*Nature.*—Tea.

Bud:

*Peduncle.*—Short: medium, caliper; erect; stiff, entirely smooth. Color: Light green.

*Before calyx breaks.*—Size: From medium to small. Form: From short to medium length; oval; with a conspicuous neck; with foliaceous appendages on the surface of the bud; with slender, bristle-like foliaceous parts extending beyond the tip of the bud equal to ¼ or more of its length.

*As calyx breaks.*—Color: From strong Red, Hue 5 R 4/12 to Strong Reddish Orange, Hue 7.5 R 5/13.

*As first petal opens.*—Size: Very small. Form: Very short; mostly globular. Color: Outside—between Strong Reddish Orange, Hue 7.5 R 6/12 and Strong Reddish Orange, Hue 7.5 R 5/13, with a small segment at base Brilliant Greenish Yellow, Hue 7.5 Y 9/8; inside—Strong Reddish Orange, Hue 7.5 R 5/13, with a small segment at base Brilliant Greenish Yellow, Hue 7.5 Y 9/8.

*Opening.*—Opens up well.

Bloom:

*Size (when fully open).*—Medium; from 3 inches to 4½ inches.

*Petalage.*—Very double (usually with no stamens showing); from 44 to 50 petals; arranged irregularly.

*Form.*—Semi-cupped and full at first, but becoming flat to cupped; petals being at first cupper somewhat inward, but later becoming flat and rolled outward at maturity.

Petals:

*Texture.*—Fairly thick; soft.

*Appearance.*—Inside: Somewhat shiny satiny. Outside: Satiny.

*Shape.*—Outside: Round. Intermediate: Round. Inside: Round.

This description of a newly opened flower was made from a rose grown outdoors during the month of October at Ontario, Calif.

*Color.*—Outer petal: Outside surface—between Vivid Red, Hue 5 R 5/13 and Deep Pink, Hue 2.5 R 6/11, but somewhat brighter, with a small segment of Brilliant Greenish Yellow, Hue 7.5 Y 9/8 at base; inside surface—between Strong Reddish Orange, Hue 7.5 R 5/13 and Strong Reddish Orange, Hue 7.5 R 6/12, but somewhat brighter, with a small segment of Brilliant Greenish Yellow, Hue 7.5 Y 9/8 at base.

*Intermediate petal.*—Outside surface: Between Strong Reddish Orange, Hue 7.5 R 5/13 and Strong Reddish Orange, Hue 7.5 R 6/12, with a small segment of Brilliant Yellow Green, Hue 2.5 GY 9/8 at base. Inside surface: Between Strong Reddish Orange, Hue 7.5 R 5/13 and Strong Reddish Orange, Hue 7.5 R 6/12, with a small segment of Brilliant Greenish Yellow, Hue 7.5 Y 9/8 at base.

*Inner petal.*—Outside surface: Between Deep Yellowish Pink, Hue 5 R 6/11 and Strong Reddish Orange, Hue 7.5 R 6/12, with a small segment of Brilliant Yellow Green, Hue 2.5 GY 9/8 at base. Inside surface: Between Strong Reddish Orange, Hue 7.5 R 5/13 and Strong Reddish Orange, Hue 7.5 R 6/12 but brighter, with a small segment of Brilliant Yellow Green, Hue 2.5 GY 9/8 at base.

This description was made from a rose that was open for three days outdoors during the month of October at Ontario, Calif.

*Color.* — Outer petal: Outside surface — between Strong Red, Hue 2.5 R 5/12 and Deep Pink, Hue 2.5 R 6/11, but brighter, with a small segment of Brilliant Greenish Yellow, Hue 7.5 Y 9/8 at base; inside surface—between Strong Red, Hue 2.5 R 5/12 and Deep Pink, Hue 2.5 R 6/11, but brighter, with a small segment of Brilliant Greenish Yellow, Hue 7.5 Y 9/8 at base. Inner petal: Outside surface—between Deep Pink, Hue 2.5 R 6/11 and Strong Pink, Hue 2.5 R 7/8, with a small segment of Brilliant Yellow, Hue 5 Y 9/9 at base; inside surface—between Deep Pink, Hue 2.5 R 6/11 and Strong Pink, Hue 2.5 R 7/8, with a small segment of Brilliant Yellow, Hue 5 Y 9/9 at base.

*General color effect.*—Newly opened flower: Between Strong Red, Hue 2.5 R 5/12 and Deep Pink, Hue 2.5 R 6/11, with some shading of Strong Reddish Orange, Hue 7.5 R 6/12. 3-days open: Between Strong Reddish Orange, Hue 7.5 R 5/13 and Strong Reddish Orange, Hue 7.5 R 6/12, with an occasional minute area on the tips considerably lighter.

*Behavior.*—Drops off cleanly.

*Flower longevity.*—On bush in garden: From 3 to 5 days in October. Cut roses grown outdoors and kept at living room temperatures: From 3 to 5 days in October.

REPRODUCTIVE ORGANS

Stamens: Medium number; arranged irregularly about pistils.

Filaments: From short to medium length; some without anthers.

*Color.*—From white to yellow.

Anthers: Very small; mostly all open at once.

*Color.*—Yellow.

Pollen: From sparse to moderate quantity.

Pistils: Medium number.

Styles: Uneven; from short to medium length; thin caliper; loosely separated.

Stigma:

*Color.*—Yellowish.

Ovaries: All protruding from calyx.

Hips: None observed.

Sepals: Permanent; moderately long; spear-shaped; curled.

*Color.*—Outside: Light green. Inside: Grayish green.

Seeds: None observed.

PLANT

Foliage:

*Leaves.*—Compound of 3, 5 and occasionally 7; abundant; moderately heavy; semi-glossy; moderately large.

*Leaflets.*—Shape: Obovate. Apex: Between obtuse and acute. Base: From round to obtuse. Margin: Simply serrate.

*Color.*—Mature: Upper surface—normal green; under surface—moderately light green, with reddish veins. Young: Upper surface—from moderately red to bronze; under surface—moderately red.

*Rachis (the supporting stem of the compound leaf).*—Medium weight. Upper side—smooth; under side—sparsely prickly.

*Stipules.*—Medium length; medium wide; with moderately short points turning out at an angle of more than 45°; recurved toward the stem.

*Disease resistance.*—Above average resistance to mildew and other rose diseases, as determined by comparison with other rose varieties grown under comparable conditions at Ontario, Calif.

Growth:

*Habit.*—Tall; bushy; much-branched.

*Growth.*—From very free to vigorous.

*Canes.*—Heavy caliper.

*Main stems.*—Color: Dull green. Large prickles: Several; from medium length to long; hooked downward; with short, broad to round base; color—gray. Small prickles: Few; color—Gray. Hairs: None.

*Branches.*—Color: Dull green. Large prickles: Several; medium long; hooked slightly downward; with short, narrow to round base; color—brown. Small prickles: Few; color—brown. Hairs: None.

*New shoots.*—Color: Dull green. Large prickles: Several; from medium length to long; hooked slightly downward; with narrow base; color—from brown to gray. Small prickles: Few. Hairs: Few; color—gray-green.

We claim:

1. A new and distinct variety of rose plant of the hybrid tea class, substantially has herein shown and described, characterized particularly as to novelty by the unique combination of an especially well-branched, tall and symmetrical plant habit, exceptionally good, heavy and semi-glossy foliage which clothes the plant well and which has excellent resistance to powdery mildew, heavy stems of sufficient strength to hold all blooms erect, with a consequent pleasing complement to the attractive foliage, large flowers which are borne both singly and in clusters of 2 to 4 flowers, with an occasional cluster of 5 flowers, a distinctive, attractive and unusual coral-orange flower color, and a moderate and pleasing tea flower fragrance.

No references cited.

ROBERT E. BAGWILL, Primary Examiner